(12) United States Patent
Rheude et al.

(10) Patent No.: US 6,541,660 B2
(45) Date of Patent: Apr. 1, 2003

(54) PROCESS FOR PREPARING $C_5$ ACETATE

(75) Inventors: Udo Rheude, Otterstadt (DE); Maximilian Vicari, Limburgerhof (DE); Werner Aquila, Mannheim (DE); Günter Wegner, Römerberg (DE); Jörg Niekerken, Holzminden (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/106,389

(22) Filed: Mar. 27, 2002

(65) Prior Publication Data

US 2002/0177730 A1 Nov. 28, 2002

(30) Foreign Application Priority Data

Apr. 5, 2001 (DE) .............................. 101 17065

(51) Int. Cl.$^7$ .................... C07C 67/38; C07C 67/36; C07C 69/66; C07C 67/05; C07C 27/10
(52) U.S. Cl. .................. 560/233; 560/175; 560/177; 560/243; 560/241.1
(58) Field of Search ................ 560/233, 175, 560/177, 243, 241.1

(56) References Cited

U.S. PATENT DOCUMENTS

| 3,732,287 A | | 5/1973 | Himmele et al. |
| 4,504,676 A | * | 3/1985 | Schnabel et al. ............ 560/244 |
| 5,932,761 A | * | 8/1999 | Omatsu et al. ............. 560/233 |

FOREIGN PATENT DOCUMENTS

| DE | 1945 479 | 3/1971 |
| DE | 24 06 058 | 10/1975 |
| DE | 33 09168 | 9/1984 |
| GB | 1487274 | 9/1977 |

OTHER PUBLICATIONS

Chem.Ing.Techn.45.Jahrg,1973 Reif et al. 646–652.

* cited by examiner

Primary Examiner—J. Parsa
(74) Attorney, Agent, or Firm—Keil & Weinkauf

(57) ABSTRACT

A process is proposed for preparing $C_5$ acetate for Vitamin A synthesis by hydroformylation of 3,4-diacetoxybut-1-ene (3,4-DABE), according to which a 3,4-DABE is used which is obtained by acetoxylation of 1,3-butadiene with acetic acid and air in the presence of a catalyst and removing by distillation the 3,4-DABE formed in this case as by-product.

8 Claims, 2 Drawing Sheets

PROCESS FOR PREPARING $C_5$ ACETATE

The invention relates to a process for preparing the $C_5$ acetate for Vitamin A synthesis.

For Vitamin A synthesis by the BASF process, from petrochemical base materials, a $C_5$ and a $C_{15}$ component are first built up, which are then combined using the Wittig reaction to form Vitamin A (see Chem. -Ing. -Techn. Vol. 45 1973, No. 10a, pp. 646–652). The $C_5$ component, for which, hereinafter, the symbol $C_5$ acetate is used, is β-formylcrotyl acetate having the structural formula below

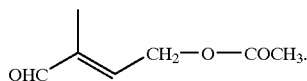

$C_5$ acetate has hitherto been obtained starting from but-2-ene-1,4-diol by esterification with acetic acid and acetic anhydride and isomerization of the resultant but-2-ene 1,4-diacetate to form 3,4-diacetoxybut-1-ene, abbreviated as 3,4-DABE below, hydroformylation of the 3,4-DABE and subsequent elimination of acetic acid.

The isomerization of but-2-ene-1,4-diol diacetate to give 3,4-DABE is described, for example, in DE-B 24 06 058. According to the process described there, the isomerization is carried out in the presence of metallic copper and/or copper(I) compounds and/or copper(II) compounds as catalysts, and in the presence of carboxylic acids. The carboxylic acid used in this case is expediently the same acid as is present in the diester which is the starting material, thus acetic acid in the case of but-2-ene-1,4-diol diacetate.

The hydroformylation of 3,4-DABE to prepare $C_5$ acetate can advantageously be performed in the presence of rhodium catalysts. Such a process is described, for example, in DE-A 19 45 479. According to this, 3,4-DABE is reacted with carbon monoxide and hydrogen, preferably in stoichiometric amounts, at temperatures of monoxide and hydrogen, preferably in stoichiometric amounts, at temperatures of from 60 to 120° C., preferably from 80 to 105° C., and at pressures from 300 to 1200 atmospheres, preferably from 500 to 700 atmospheres, in the presence of rhodium carbonyl complexes. The rhodium carbonyl complexes can be prepared separately before the hydroformylation reaction, or the starting materials for this can be fed to the hydroformylation, the rhodium carbonyl complexes forming in situ. The catalyst concentration is preferably from 0.00005 to 0.05% by weight, particularly preferably 0.0001 to 0.01% of rhodium, calculated as metal, based on the amount of the starting material 3,4-DABE used. The reaction can be carried out without conjoint use of inert solvents, and also in the presence of inert solvents such as hydrocarbons, for example benzene, cyclohexane, xylene, hexane, ethers such as diethyl ether, tetrahydrofuran or dioxane, or esters, such as ethyl acetate.

It is an object of the present invention to improve the space-time yield of the hydroformylation reaction of 3,4-DABE to give $C_5$ acetate and thus to improve the economic efficiency of the process.

We have found that this object is achieved by a process for preparing $C_5$ acetate for Vitamin A synthesis by hydroformylation of 3,4-diacetoxybut-1-ene (3,4-DABE).

The invention comprises using a 3,4-DABE-containing stream which is obtained by acetoxylation of 1,3-butadiene with acetic acid and air in the presence of a catalyst and removing by distillation the 3,4-DABE formed in this case as by-product.

It has surprisingly been found that 3,4-DABE, which is produced as by-product of the acetoxylation of butadiene, can not only be used as a product of value for further processing to form $C_5$ acetate, but, in addition, leads to a considerably better result, in particular an improved space-time yield, in the process for preparing the $C_5$ acetate, in comparison with a 3,4-DABE prepared starting from but-2-ene-1,4-diol.

Starting from 1,3-butadiene, 1,4-butanediol is prepared in industrial quantities, which is a base product of the chemical industry. For this, 1,3-butadiene is acetoxylated in a first process step with acetic acid and air. In this reaction, in addition to the 1,4-diacetoxybutene wanted for the further processing to form the 1,4-butanediol, the isomeric 3,4-DABE is also produced in a considerable proportion, frequently 15% by weight or more.

A process for the acetoxylation of 1,3-butadiene and for removing by distillation the 3,4-DABE formed as by-product is described, for example, in DE-A 33 09 168. According to this, the acetoxylation is carried out in the presence of catalysts and at elevated temperatures and pressures. As catalysts, palladium and/or platinum-containing catalysts are listed as preferred, which are in particular supported. The active catalyst composition can also comprise, in addition to palladium or platinum, other metals, such as Te, Cu, Sb, Se or Bi. Preference is given to a temperature range from 80 to 120° C. and a pressure range from 1 to 100 bar. From the acetoxylation reaction mixture, low-boilers are first removed, in particular unreacted 1,3-butadiene, then the high-boiling fraction, which predominantly comprises 1,4-DABE and 3,4-DABE, is fractionally distilled, preferably at bottom temperatures from 150 to 180° C., corresponding to column pressures of from 60 to 80 mbar. A stream predominantly comprising 3,4-DABE is removed which, according to the statements of DE-A 33 09 168, is recirculated in whole or in part to the acetoxylation reactor.

According to the process of the present invention, the 3,4-DABE-containing stream obtained by removal by distillation from the product of acetoxylation of 1,3-butadiene is used for further processing to form $C_5$ acetate.

In this case, there are no restrictions with respect to the actual process conditions of the acetoxylation reaction. This can be carried out particularly preferably, as described above, by the process of DE-A 33 09 168.

Also, there are in principle no restrictions with respect to removing a 3,4-DABE-containing stream by distillation from the acetoxylation reaction mixture.

Advantageously, the acetoxylation reaction mixture can be fed to a distillation column in its bottom region and the 3,4-DABE-containing stream can be removed from the distillation column as a liquid sidestream.

The distillation column is preferably operated at reduced pressure, in order to avoid decomposition reactions or conversion reactions. Preference is given to a bottom temperature in the range from 110 to 190° C., in particular from 120 to 150° C., particularly preferably 130° C., and a pressure in the range from 5 to 200 mbar, in particular from 20 to 50 mbar, particularly preferably 30 mbar.

Alternatively to removing the 3,4-DABE-containing stream as a liquid sidestream takeoff from a distillation column, it is possible to use two distillation columns connected in series, the overhead stream from the first distillation column being fed to the second distillation column and a 3,4-DABE-containing stream being taken off from the bottom of the second distillation column.

With respect to the internals which are active in separation for the distillation column(s), there are in principle no restrictions, but particular preference is given to structured arranged packings of metal or ceramic materials.

The 3,4-DABE-containing stream removed by distillation frequently has a 3,4-DABE content in the range from 75 to 90% by weight, preferably approximately 85%, based on the total weight. In addition, the corresponding monoacetates, that is to say 3-hydroxy-4-acetoxybut-1-ene and 3-acetoxy-4-hydroxybut-1-ene are frequently present at a higher content by weight. The two above-mentioned components and mixtures thereof are referred to below by the combined term 3,4-HABE.

The 3,4-DABE-containing stream, before the hydroformylation to form the $C_5$ acetate, is preferably fed to a reesterification with acetic anhydride, acetic acid or ketene, in which case the 3,4-HABE content present therein is reesterified to give 3,4-DABE.

The 3,4-DABE-containing stream, which is possibly subjected to a reesterification, can be purified by distillation or fed immediately to the hydroformylation to form the $C_5$ acetate. Expediently, the acetic acid released from the acetic anhydride, or the resultant reaction water, if the esterification is carried out with acetic acid, is removed.

The hydroformylation is performed in a known manner using carbon monoxide and hydrogen, preferably in the presence of rhodium carbonyl complexes as catalysts, at elevated temperature and elevated pressure. Particularly preferably, the hydroformylation is carried out by the process of DE-A 19 45 479 described at the outset.

The invention is described in more detail below with reference to a figure and an example.

In the following diagram in FIG. 1, the kinetics of the hydroformylation reaction of 3,4-DABE are shown, where the lower curve, II, was recorded for a hydroformylation reaction in which a 3,4-DABE conventionally prepared from but-2-ene-1,4-diol was used, whereas the upper curve, I, was recorded for a hydroformylation reaction in which, in accordance with the inventive process, the starting material used was 3,4-DABE obtained by removal by distillation from the acetoxylation product of 1,3-butadiene and subsequent reesterification of the resultant 3,4-HABE.

The starting material for the comparative experiment (curve II) was obtained by acetylation of but-2-ene-1,4-diol and subsequent isomerization using glacial acetic acid and copper(II) acetate, corresponding to Example 3 of DE-B 24 06 058.

Both starting materials, that is to say both for the comparative experiment and for the example according to the inventive process, comprised from approximately 95 to 98% 3,4-DABE and a plurality of minor components which were not clarified in more detail.

Figure 2:
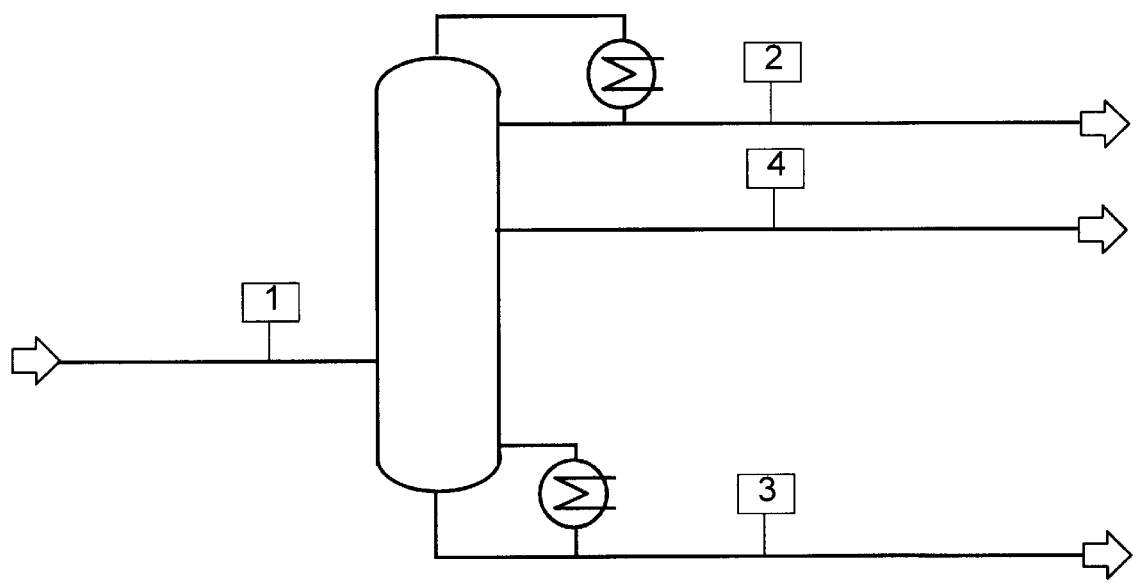
FIG. 2 shows the diagram of a distillation column for fractionating the stream 1 obtained from the acetoxylation of 1,3-butadiene to produce a 3,4-DABE-containing stream 4 via a sidestream takeoff of the distillation column.

In contrast, for the hydroformylation reaction by the inventive process, whose kinetics are shown in curve I, a 3,4-DABE-containing stream was used which was obtained from the catalytic acetoxylation of 1,3-butadiene and was then fractionated by distillation. In the following FIG. 2, the fractionation of the acetoxylation mixture (stream I) is shown in a distillation column, with production of a 3,4-DABE-containing stream (4).

The distillation column is equipped, as is conventional, with a bottoms reboiler and a condenser at the column top, which are shown diagrammatically. Stream 2 designates the low-boiling mixture taken off at the column top and stream 3 the high-boiling mixture taken off from the column bottom, which is processed in further processing steps to give 1,4-butanediol.

The composition of the streams in kg/kg is listed in the table below.

| Stream No. | 1 | 2 | 3 | 4 |
|---|---|---|---|---|
| Acetic acid | 0.0290 | 0.9638 | 0.0000 | 0.0090 |
| cis-1,4-Diacetoxybutene | 0.1140 | 0.0000 | 0.1318 | 31 ppm |
| trans-1,4-Diacetoxybutene | 0.7290 | 0.0000 | 0.8427 | 5 ppm |
| 3,4-DABE | 0.0990 | 0.0020 | 0.0125 | 0.8325 |
| Monoacetoxybutene | 0.0010 | 0.0337 | 0.0000 | 179 ppm |
| 1,4-Hydroxyacetoxybutene | 0.0020 | 0.0000 | 0.0023 | 2 ppm |
| 3,4-HABE | 0.0180 | 0.0005 | 0.0014 | 0.1582 |
| Acetoxycrotonaldehyde | 0.0080 | 0.0000 | 0.0092 | 17 ppm |
| Amount based on feed | 100% | 3% | 87% | 11% |

The predominantly 3,4-DABE-containing stream 4 was reesterified with acetic anhydride, purified by distillation and then, at a content of from approximately 95 to 98% DABE, was used for the hydroformylation reaction to give $C_5$ acetate.

Figure 1:
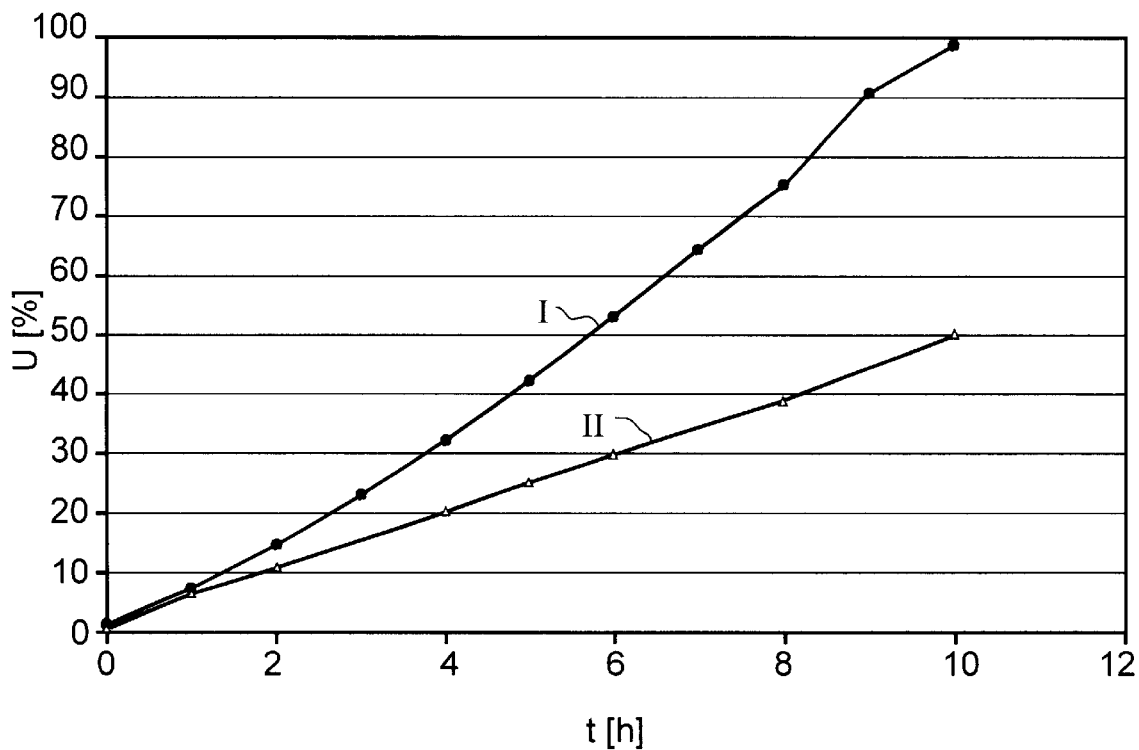
FIG. 1 shows the reaction kinetics of the hydroformylation reaction, that is to say the conversion rate U in percent as a function of the reaction time t in hours for the inventive process (curve I) compared with the prior art (curve II)

The representation in FIG. 1 shows that, using the inventive process, a conversion rate of approximately 50% was reached after about 5.5 hours (curve I), while for the same conversion rate of 50% by the prior art, virtually twice the time, 10 hours, was required (FIG. II).

We claim:

1. A process for preparing $C_5$ acetate for Vitamin A synthesis by hydroformylation of 3,4-diacetoxybut-1-ene, (3,4-DABE), which comprises using a 3,4-DABE-containing stream which is obtained by acetoxylation of 1,3-butadiene with acetic acid and air in the presence of a catalyst and removing by distillation the 3,4-DABE formed in this case as by-product.

2. A process as claimed in claim 1, wherein the 3,4-DABE-containing stream is removed as liquid sidestream from a distillation column.

3. A process as claimed in claim 1, wherein the distillation column is operated at a bottom temperature in the range from 110 to 190° and at a pressure of from 5 to 200 mbar.

4. A process as claimed in claim 1, wherein a stream comprising from 75 to 90% by weight of 3,4-DABE is removed by distillation.

5. A process as claimed in claim 1, wherein 3,4-DABE is reacted with carbon monoxide and hydrogen in the presence of carbonyl complexes of rhodium at elevated temperature and elevated pressure.

6. A process as claimed in claim 4, wherein a stream comprising approximately 85% by weight of 3,4-DABE is removed by distillation.

7. A process as claimed in claim 3, wherein the distillation column is operated at a bottom temperature in the range from 120 to 150° C. and at a pressure of from 20 to 50 mbar.

8. A process as claimed in claim 3, wherein the distillation column is operated at a bottom temperature of 130° C. at a pressure of about 30 mbar.

* * * * *